US008851018B2

(12) United States Patent
Rapoport et al.

(10) Patent No.: US 8,851,018 B2
(45) Date of Patent: Oct. 7, 2014

(54) MASK FOR ANALYZED MAMMALS

(75) Inventors: Uri Rapoport, Moshav Ben Shemen (IL); Itzchak Rabinovitz, Nes Ziona (IL)

(73) Assignee: Aspect Imaging Ltd, Shoham (IL)

( * ) Notice: Subject to any disclaimer, the term of this patent is extended or adjusted under 35 U.S.C. 154(b) by 274 days.

(21) Appl. No.: 13/241,344

(22) Filed: Sep. 23, 2011

(65) Prior Publication Data

US 2012/0073509 A1  Mar. 29, 2012

Related U.S. Application Data

(60) Provisional application No. 61/386,595, filed on Sep. 27, 2010.

(51) Int. Cl.
  *A01K 1/03* (2006.01)
  *A61D 3/00* (2006.01)
  *A61D 7/04* (2006.01)

(52) U.S. Cl.
  CPC ... *A61D 7/04* (2013.01); *A61D 3/00* (2013.01)
  USPC .......................................... 119/420; 119/752

(58) Field of Classification Search
  USPC ......... 119/420, 752, 417; 128/206.21, 206.22
  See application file for complete search history.

(56) References Cited

U.S. PATENT DOCUMENTS

| 2,960,985 | A | * | 11/1960 | Wiese, Jr. ................. 128/203.25 |
| 3,739,751 | A | * | 6/1973 | Mohr et al. .................... 119/752 |
| 4,332,244 | A | * | 6/1982 | Levy et al. ............... 128/205.25 |
| 4,520,808 | A | * | 6/1985 | LaBauve .................. 128/200.14 |
| 4,633,890 | A | | 1/1987 | Carden |
| 5,676,133 | A | * | 10/1997 | Hickle et al. ............. 128/205.12 |
| 6,363,931 | B1 | | 4/2002 | Dellenbusch |
| 2001/0035181 | A1 | * | 11/2001 | Elkins ....................... 128/200.21 |
| 2004/0216737 | A1 | | 11/2004 | Anderson et al. |
| 2007/0238946 | A1 | * | 10/2007 | Chiodo ......................... 600/407 |
| 2010/0101500 | A1 | * | 4/2010 | Sannie et al. ................. 119/420 |
| 2011/0071388 | A1 | * | 3/2011 | Yared et al. .................... 600/425 |
| 2013/0061812 | A1 | * | 3/2013 | Chiodo ......................... 119/420 |

* cited by examiner

Primary Examiner — Son T Nguyen
(74) Attorney, Agent, or Firm — The Law Office of Michael E. Kondoudis (57) ABSTRACT

An encapsulatable life support mechanism (ELSM) for an analyzed animal, including: a cradle or bed adapted by means of size and shape to accommodate the animal; an anesthetization gas mask (AGM) characterized by a cup with conic cross section, comprising a plurality of apertures located at the outer circumference of the cup; a fluid supplying mechanism (FSM) in which the AGM is placed, the FSM is in a continuous fluid communication with (i) an anesthetization gas inlet positioned outside the ELSM and an outlet located within the ELSM; (ii) an air suction scavenging device positioned outside the ELSM and a mask and an air suction outlet located within the ELSM; and a plurality of (iii) air conditioning tubes; and an airtight shell enveloping the same. The airtight ELSM prevent leakage of anesthetization gas.

8 Claims, 6 Drawing Sheets

MASK FOR ANALYZED MAMMALS

FIELD OF THE INVENTION

The present invention generally pertains to masks for behavior of mammals, such as anesthetized mice and rats, scanned within an MRI device. The invention also relates to methods of treating mammals during the study thereof and to methods for reducing exposure of laboratory personnel to hazardous fluids.

BACKGROUND

MRI-compatible anesthesia gas masks for animals and MRI-compatible platforms for animal surgery are commercially available items; see for example products of Stoelting Co (US), 2Biological Instruments (IT) etc. As designed by their producers, these gas anesthesia platforms and mouse, rat, dog etc. masks provide easy positioning of an animal during anesthesia and surgery and often allow for anesthetization and positioning of the animal outside of a stereotaxic device and for dorsal surgery. The animal's teeth are usually placed over an incisor bar and the mask slid forward until the cone fits snugly around the animal's nose, so that no nose clamp is required. The platform is then lifted onto an appropriate stereotaxic device, providing positioning of the animal. The head of the animal is not perfectly conical, however. Eyes, ears and other organs of the animal do not perfectly fit the conical mask, and hazardous leakage of anesthetization gas often occurs within the close environment of the laboratory. Cases in which laboratory personnel collapsed after breathing anesthetization gas applied to experimental animals have been reported in the literature.

US patent application 2004/0216737 discloses an anesthesia system for administering an anesthetic gas to the nose of an animal. The anesthesia system comprises a mask having a receptacle adapted to surround and form a fluid path to the animal's nose; a breather enclosure forming an air exchange chamber, the breather enclosure comprising a connector configured for coupling with the mask to connect the receptacle and air exchange chamber in fluid communication; an inlet hub extending inside the air exchange chamber and forming an inlet port through a wall in the breather enclosure, the inlet port being adapted to convey the anesthetic gas into the chamber and to the mask; and a check valve connected with the inlet hub and extending within the air exchange chamber, the check valve being operable in response to relative pressure in the air exchange chamber between an open position, which permits anesthetic gas to enter the air exchange chamber, and a closed position, which substantially prevents anesthetic gas from entering the air exchange chamber, wherein the check valve moves to the open position in response to vacuum pressure created when the animal inhales, the check valve being normally biased in the closed position.

U.S. Pat. No. 6,363,931 discloses an occluder for supporting and preventing escape of anesthesia gases through face masks when not in use, comprising: a C-shaped support base with a flat base plate adapted to fit beneath a surgical mattress, a side plate located in a plane normal to that of the base plate having a bottom edge contiguous with the base plate and having a height equal to the thickness of a standard surgical mattress, and a top plate contiguous with an upper edge of the side plate, the top plate being in a plane parallel to that of the base plate; and a solid cylindrical support shaft supported on and extending upwardly from the top plate, the cylindrical support shaft having a main body portion approximately 15 mm in diameter.

U.S. Pat. No. 4,633,890 discloses an apparatus for preventing the undesirable egress of anesthetic gas into ambient atmosphere, comprising a tube having one end connected to an anesthesia machine and its second end being a free end; the anesthesia machine supplying anesthetic gas to the tube; the free end being removably connectable to a breathing passage of a patient; an obturator post connected to the anesthesia machine and constructed to sealingly engage the free end, for preventing the undesirable egress of the anesthetic gas into the atmosphere of an operating theater when the free end is disconnected from the breathing passage; and a bore passing through the obturator post and communicating with exhaust means.

None of the above provides a simple solution for anesthetization and precise positioning of the animal within an MRI device. Hence an MRI-compatible and safe mask would fulfill a long felt need.

BRIEF SUMMARY

It is thus one object of the invention to disclose an anesthetization gas mask (AGM) characterized by a cup with conic cross section, comprising a plurality of apertures located at the outer circumference of the cup.

Another object of the invention is to disclose the AGM as defined above, wherein the mask is made of MRI-compatible materials.

Another object of the invention is to disclosed the AGM as defined above, wherein the MRI-compatible materials are polymers.

Another object of the invention is to disclose the AGM as defined above, wherein the mask is adapted by means of size and shape, to ensure anesthetization of animals.

Another object of the invention is to disclosed the AGM as defined above, wherein said animals are laboratory animals.

Another object of the invention is to disclose an anesthetization system comprising an AGM as defined above, a fluid supplying mechanism (FSM) accommodating the same, wherein the FSM is in continuous fluid communication with the anesthetization gas inlet and outlet, and an air suction outlet.

Another object of the invention is to disclose an anesthetization system comprising an AGM as defined above, wherein the system further comprises a mask maneuvering mechanism comprising an adjustment knob in connection with the mask, the knob is adapted to ensure that the mask remains in a predefined location within a housing of the FSM.

Another object of the invention is to disclose an encapsulatable life support mechanism (ELSM) for an analyzed animal. The ELSM comprises a cradle or bed adapted by means of size and shape to accommodate the animal; an anesthetization gas mask (AGM) characterized by a cup with a substantially conical cross section, comprising a plurality of apertures located at the outer circumference of the cup; a fluid supplying mechanism (FSM) in which the AGM is placed, the FSM is in a continuous fluid communication with (i) an anesthetization gas inlet positioned outside the ELSM and an outlet located within the ELSM; (ii) an air suction scavenging device positioned outside the ELSM and a mask and an air suction outlet located within the ELSM; and optionally (iii) a plurality of air conditioning tubes; and an airtight shell enveloping the same. The airtight ELSM prevents leakage of anesthetization gas from the ELSM outwardly to the laboratory; provides thermal isolation between ambient air and the air-conditioned animal environment; and prevents accidental spillage of hazardous materials such as, e.g., radioactive agents, outside the environment in which the animal is accommodated.

Another object of the invention is to disclose an MRI-compatible ELSM and an ELSM wherein the AGN, FSM and mechanisms thereof are adapted by means of size and shape, to ensure anesthetization of animals.

Another object of the invention is to disclose and MRI-compatible ELSM, and an ELSM wherein the AGN, FSM and mechanisms thereof are adapted by means of size and shape, to ensure anesthetization of animals, wherein said animals are laboratory animals.

Another object of the invention is to disclose a mouse handling system (MHS) comprising an encapsulatable life support mechanism (ELSM) for an analyzed animal; the MHS is a maneuverable elongated device, characterized by a proximal portion, held outside the MRI device, and comprises at least one inner shaft and at least one outer shaft, the at least one outer shaft telescopically maneuverable along the at least one inner shaft to provide a telescopic mechanism of variable (proximal-) length; the MHS is further characterized by a distal portion comprising the ELSM, wherein the distal ELSM is rotatable and/or linearly reciprocatable along the main longitudinal axis of the shafts by means of the maneuverable telescopic mechanism of the proximal portion.

Another object of the invention is to disclose an MRI-compatible MHS and an MHS wherein the AGN, FSM and mechanisms thereof are adapted by means of size and shape, to ensure anesthetization of animals.

Another object of the invention is to disclose an MRI-compatible MHS and an MHS wherein the AGN, FSM and mechanisms thereof are adapted by means of size and shape, to ensure anesthetization of animals, wherein said animals are laboratory animals.

Another object of the invention is to disclose an MRI-compatible ELSM and an ELSM wherein the AGN, FSM and mechanisms thereof are adapted by means of size and shape, to ensure anesthetization of animals.

Another object of the invention is to disclose an MRI-compatible ELSM and an ELSM wherein the AGN, FSM and mechanisms thereof are adapted by means of size and shape, to ensure anesthetization of animals, wherein said animals are laboratory animals.

Another object of the invention is to disclose a safe method for forming an airtight capsule to prevent leakage of anesthetization gas from the gas supply inlets to the laboratory; and/or to prevent accidental spillage of hazardous materials, e.g. radioactive agents, outside of the environment enclosing the animals; the method comprising steps of providing a mouse handling system (MHS) which is a maneuverable elongated device comprising an encapsulatable life support mechanism (ELSM) for the analyzed animal; characterizing the same by a proximal portion, held outside the MRI device, comprising at least one inner shaft and at least one outer shaft, the at least one outer shaft telescopically maneuverable along the at least one inner shaft to provide a telescopic mechanism of variable (proximal-) length; and further characterizing the same by a distal portion comprising the ELSM. The distal ELSM is rotatable and/or linearly reciprocatable along the main longitudinal axis of the shafts by means of the maneuverable telescopic mechanism of the proximal portion.

Another object of the invention is to disclose a safe method for preventing leakage of anesthetization gas from the gas supply inlets to the laboratory. The method comprises steps of providing an anesthetization gas mask (AGM); further characterizing the same by a cup with substantially conical cross section; and providing plurality of apertures located at the outer circumference of the cup.

DETAILED DESCRIPTION

The following description is provided in order to enable any person skilled in the art to make use of the invention and sets forth the best modes contemplated by the inventor of carrying out this invention. Various modifications, however, will remain apparent to those skilled in the art, since the generic principles of the present invention have been defined specifically to provide a mask for analyzed mammals and methods using the same.

The term 'Magnetic Resonance Device' (MRD) specifically applies hereinafter to any Magnetic Resonance Imaging (MRI) device, any Nuclear Magnetic Resonance (NMR) spectroscope, any Electron Spin Resonance (ESR) spectroscope, any Nuclear Quadruple Resonance (NQR) spectroscope or any combination thereof. The MRD hereby disclosed is optionally a portable MRI device, such as the ASPECT Magnet Technologies Ltd commercially available devices, or a commercially available non-portable device. Moreover, the term 'MRD' generally refers in this patent to any medical device, at least temporary accommodating an anesthetized animal.

The term 'about' refers herein to a value of ±25% of the defined measure.

Figure 1:
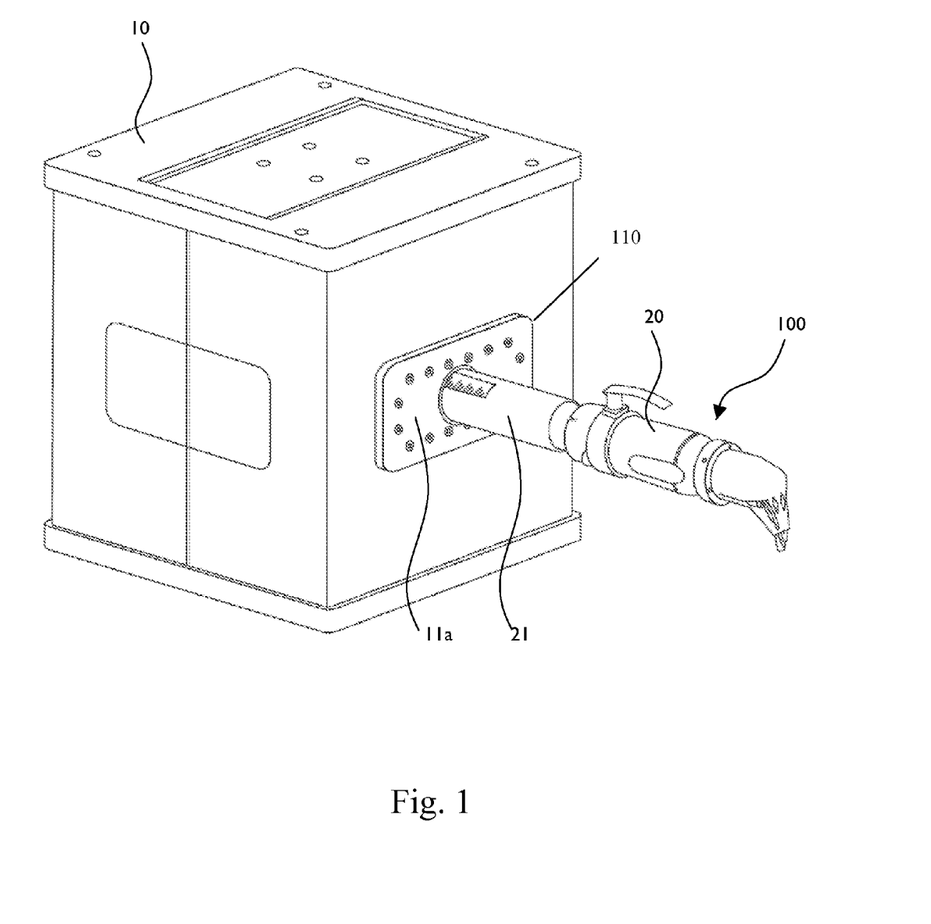
FIG. 1 shows an MRD device including at least one port for use inserting therein a Mouse Handling System (MHS), in accordance with a preferred embodiment of the present invention.

Reference is now made to FIG. 1, schematically illustrating, not to scale, an MRI device, such as an MRD 10, comprising at least one port 110. A mouse handling system (MHS, 100), which is a maneuverable elongated device, is inserted through the port 10. In preferred embodiments, the MHS 100 is characterized by a substantially circular cross-section and a proximal portion 20, which is located outside the MRD 10. The MHS 100 further includes a shaft 21, and a distal portion 30 (see FIG. 2). The maneuverable MHS 100 is rotatable about longitudinal axis of the shaft 21 (FIGS. 1 and 2) and is translationally maneuverable parallel to the shaft 21. The proximal end 20 is slideable over the shaft 21, providing a telescopic mechanism of variable length.

Figure 2:
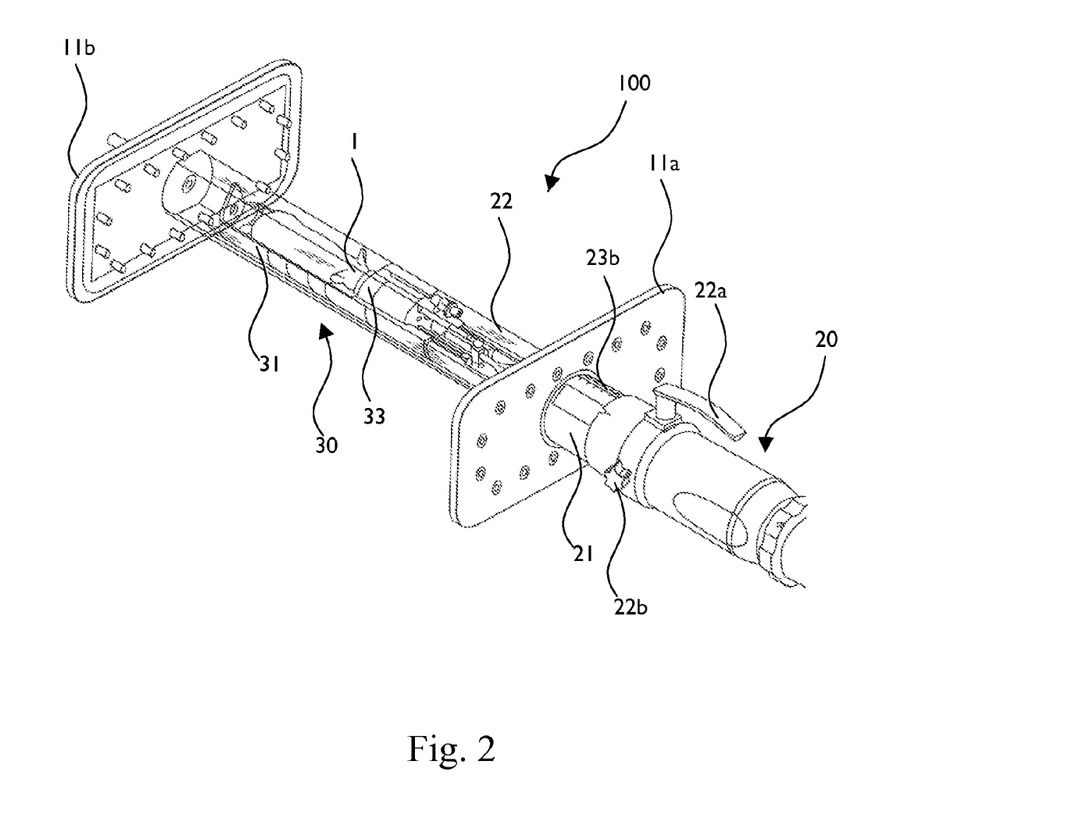
FIG. 2 shows the MHS including sealing flanges and a mouse holding portion, in accordance with a preferred embodiment of the present invention.

Reference is now made to FIG. 2, schematically illustrating, not to scale, the MHS 100 includes the flange 11a and a flange 11b, located at a distal opposite end of the MHS 100.

The MHS 100 is inserted into port 110 of the MRD 10. The proximal portion 20 of MHS 100 comprises a plurality of levers and handles (22a and 22b) which lock the location of the maneuverable MHS 100, within the MRD 10 and a connection mechanism adapted to communicate the encapsulated environment of the distal portion 30 with the proximal portion 20, by means of a plurality of fluid-connecting pipes (not shown here). The proximal end 20 of MHS 100 comprises a plurality of indicia, such as a rotation indication 23b, positioned on the shaft 21 indicates the angular and translational relative position of the MHS 100 with respect to MRD 10. According to one embodiment of the invention, the proximal portion 20 of the MHS 100 includes an airtight capsule 30 comprising a shell 22, an animal bed or cradle 31, for locating an animal 1 to be studied as well as a fluid supplying mechanism 33. The role of shell 22, inter alia, is (i) to form an airtight capsule to prevent leakage of anesthetization gas from the gas supply inlets to the laboratory environment; (ii) to provide thermal isolation between the laboratory environment the air-conditioned environment surrounding the animal in the shell 22 and the laboratory environment; and (iii) to prevent accidental spillage of hazardous materials, e.g. radioactive agents outside the shell 22 surrounding the animal.

Figure 3:
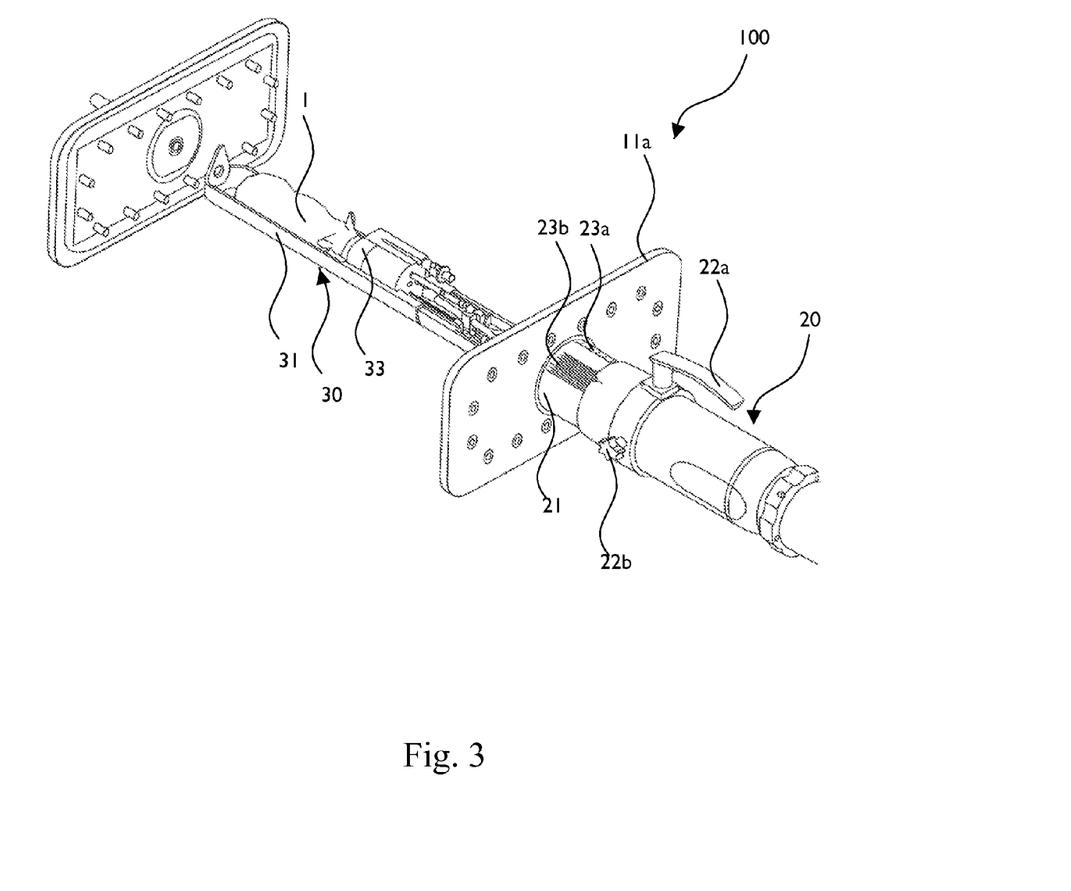
FIG. 3 shows the details of the proximal portion of the MHS, in accordance with a preferred embodiment of the present invention.

Reference is now made to FIG. 3, schematically illustrating, not to scale, the proximal portion 20 of MHS 100, which comprises the shaft 21 upon which a translational scale 22a and a rotation scale 23b are positioned, and a distal portion 30 (here without shell 20), where mouse 1 is lying thereon the cradle 31.

Figure 4:
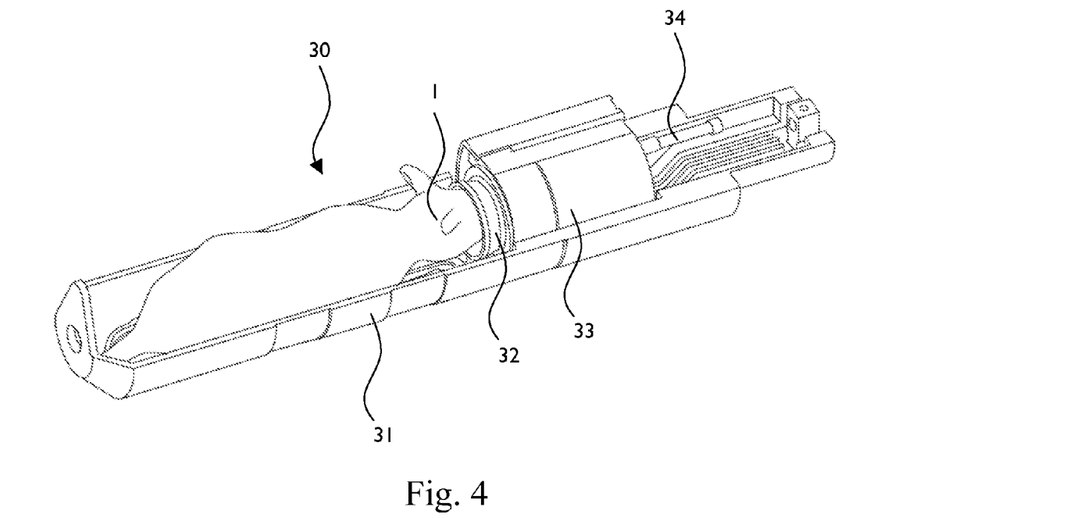
FIG. 4 shows the location of the mouse within the MHS, in accordance with a preferred embodiment of the present invention.

Reference is now made to FIG. 4, schematically illustrating, not to scale, the distal portion 30. The mouse 1 is immobilized on the cradle 31 and its head is placed within a mask 32. The position of the mask 32 within a housing 33 is determined by means of rotatable rod 34.

Figure 5:
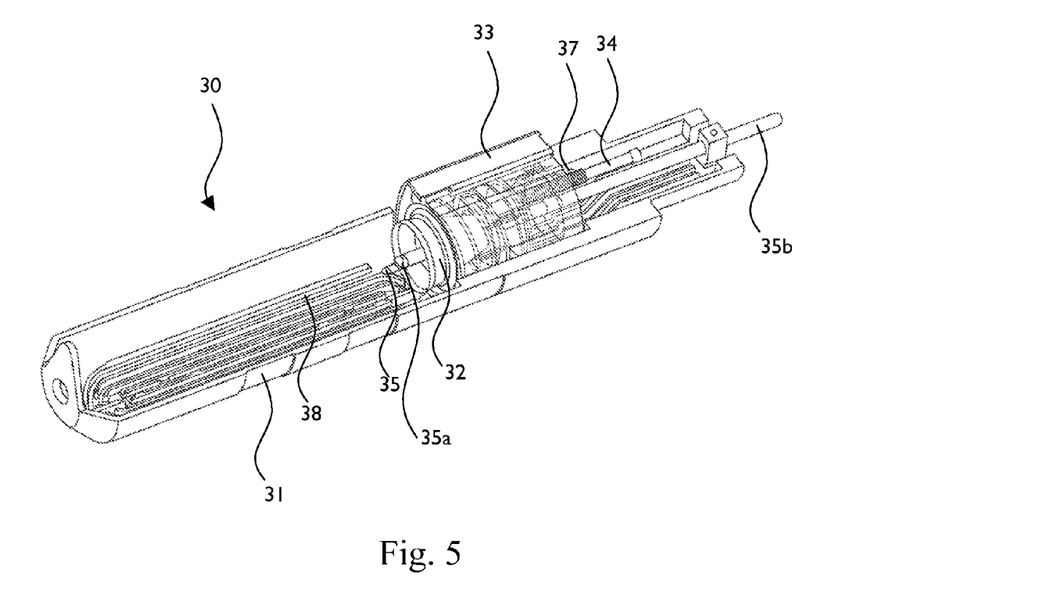
FIG. 5 shows the details of the distal portion of the MHS, in accordance with a preferred embodiment of the present invention.

Reference is now made to FIG. 5, schematically illustrating, not to scale, the distal portion 30. According to one embodiment of the invention, the cradle 31 comprises a heating/cooling mechanism 38. Mask 32 may comprise mouthpiece 35 and anesthetization gas outlet 35a in fluid communication with anesthetization gas inlet 35b. Mask 32 is located within a housing of fluid supply mechanism 33, and its position is accurately determined by rod 34.

Anesthetization gas is supplied to the animal via outlet 35a with flow f ($cm^3$/sec). Air suction is provided from the mask 32 and apertures thereon (not shown) via inner portion of the housing 33 to suction outlet 37 with flow F, wherein F>>f. Hence, leakage of anesthetization gas from outlet 35a and the inner portion of capsule 22 to the external environment of the laboratory is avoided.

Figure 6A:
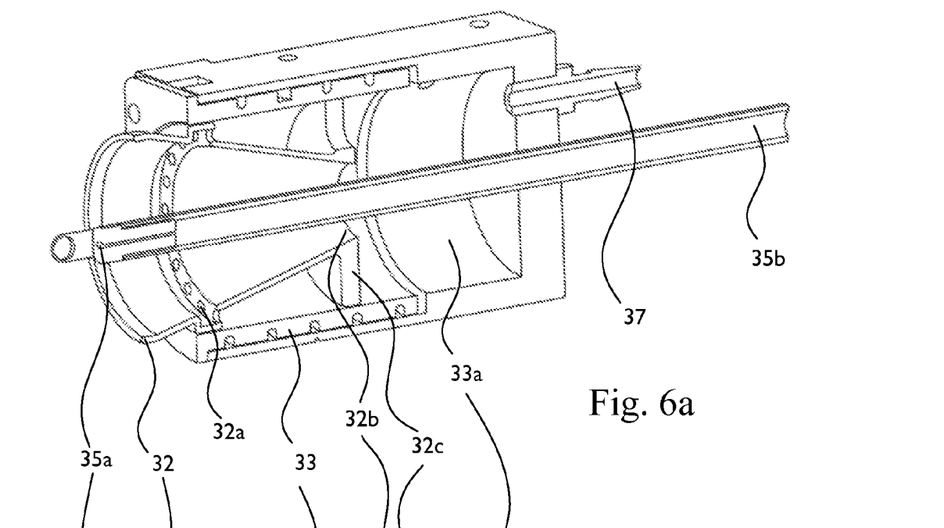
FIGS. 6a and 6b show the flushing air device, in accordance with a preferred embodiment of the present invention.
Figure 6B:
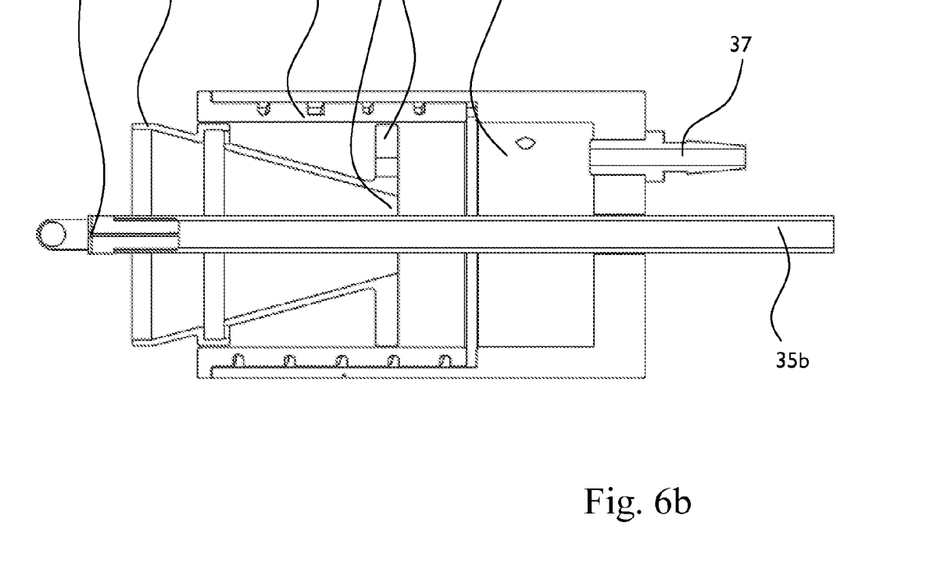

Reference is now made to FIGS. 6a and 6b, schematically illustrating, not to scale, the facilitated flow of flushing air device. The flow begins from the behind anesthetization gas inlet 35b and passes around the animal's head via mask 32 and plurality of apertures 32a into the Bernoulli-type orifice 32b (orifice 32b is narrow relative to the widest diameter of the mask), via a hollow chamber 33a of the housing 33, to an outlet 37 and to a gas scavenger located outside the MRD.

Figure 7:
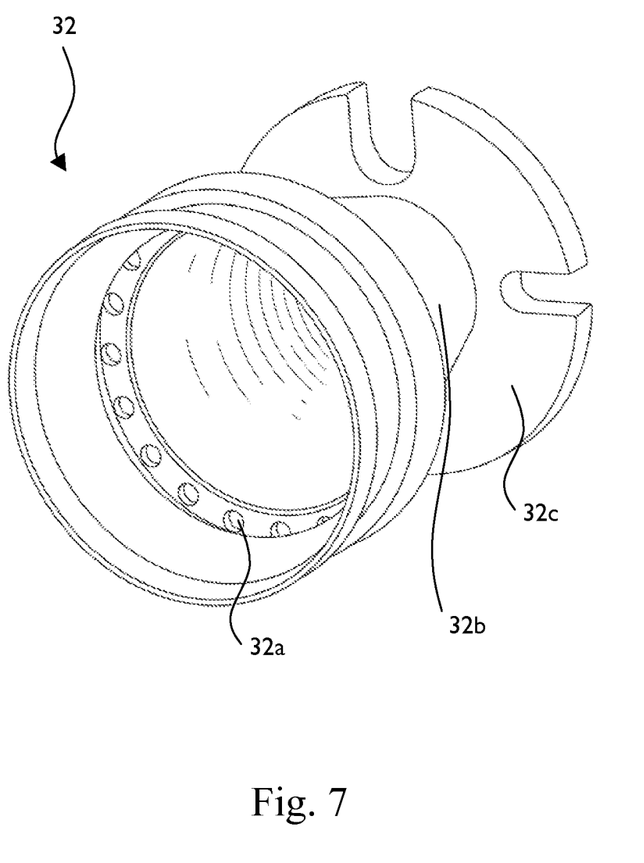
FIG. 7 shows a conic mask 32, in accordance with a preferred embodiment of the present invention.

Reference is finally made to FIG. 7, schematically illustrating, not to scale, a conic mask 32 and its plurality of apertures 32a, a Bernoulli-type orifice 32b (orifice 32b is narrow relative to the widest diameter of mask), and adapter 32c which couples the mask 32 to the housing 33 in a maneuverable manner. The role of apertures 32a located in the outer circumference of the mask is to ensure effective flushing of air due to the irregular geometry of the animal's head 1, and to avoid blocking of air suction by the animal's body parts and fur.

Examples of various features/aspects/components/operations have been provided to facilitate understanding of the disclosed embodiments of the present invention. In addition, various preferences have been discussed to facilitate understanding of the disclosed embodiments of the present invention. It is to be understood that all examples and preferences disclosed herein are intended to be non-limiting.

Although selected embodiments of the present invention have been shown and described individually, it is to be understood that at least aspects of the described embodiments may be combined.

Although selected embodiments of the present invention have been shown and described, it is to be understood the present invention is not limited to the described embodiments. Instead, it is to be appreciated that changes may be made to these embodiments without departing from the principles and spirit of the invention, the scope of which is defined by the claims and the equivalents thereof.

We claim:

1. An encapsulatable life support mechanism (ELSM) for an analyzed animal, comprising:
    a. a cradle or bed selected to be of size and shape to accommodate said animal;
    b. an anesthetization gas mask (AGM) comprising: a hollow, generally cone-shaped main piece comprising a wide portion, a narrow end and an interior space; said narrow end comprising an orifice having a diameter; said wide portion comprising a central opening surrounded by a ring, said ring having an inner circumference forming said central opening and an outer circumference in physical connection with a single internal circumference of said generally cone-shaped main piece, said single internal circumference in the wide portion of said generally cone-shaped main piece; said ring comprising a plurality of apertures providing direct fluid connection between said interior space and points external to said generally cone-shaped main piece;
    c. a fluid supplying mechanism (FSM) in which said AGM is placed, said FSM in continuous fluid communication with (i) an anesthetization gas inlet positioned outside said ELSM and an outlet located within said ELSM; (ii) an air suction scavenging device positioned outside said ELSM and said mask, and an air suction outlet located within said ELSM; and (iii) a plurality of air conditioning tubes; and
    d. an airtight shell enveloping said ELSM, said airtight shell adapted to (i) prevent leakage of anesthetization gas from said ELSM outward to a laboratory; and (ii) avoid accidental spillage of hazardous materials from said airtight ELSM to said laboratory,
    wherein said airtight shell is adapted to provide thermal isolation between ambient air in said laboratory and air-conditioned animal environment,
    wherein, when a mammal's head is positioned in said central opening, said apertures, said interior space and said orifice comprise a direct open fluid connection between said external points, said interior of said mask, and points external to said narrow end, and
    wherein said orifice comprises a Bernoulli-type orifice.

2. The AGM of claim 1, wherein said mask is made of MRI-compatible materials, said MRI-compatible materials being selected from a group consisting of polymers.

3. The AGM of claim 1, further comprising a mask maneuvering mechanism comprising an adjustment rod in connection with said mask, said adjustment rod adapted to ensure that said mask is located in a predefined location within a housing of said FSM.

4. The ELSM according to claim 1, wherein said ELMS is an MRI-compatible ELSM.

5. The ELSM according to claim 4, wherein said AGM, said FSM and mechanisms thereof are selected to be of a size and a shape to ensure anesthetization of animals, said animals selected from a group consisting of laboratory animals.

6. The ELSM according to claim 1, wherein said AGM, said FSM and mechanisms thereof are selected to be of a size and a shape to ensure anesthetization of animals, said animals selected from a group consisting of laboratory animals.

7. The AGM of claim 1, further comprising a mask maneuvering mechanism that includes an adjustment rod placeable within said interior of said mask, the diameter of said adjustment rod being smaller than said diameter of said adjustment rod, said adjustment rod locatable in at least one predefined location within said FSM.

8. A safe method for preventing leakage of anesthetization gas from gas supply inlets to a laboratory, comprising:
 a. providing a cradle or bed selected to be of size and shape to accommodate said animal; an anesthetization gas mask (AGM) comprising: a hollow, generally cone-shaped main piece comprising a wide portion, a narrow end and an interior space; said narrow end comprising an orifice having a diameter; said wide portion comprising a central opening surrounded by a ring, said ring having an inner circumference forming said central aperture and an outer circumference in physical connection with a single internal circumference of said generally cone-shaped main piece, said single internal circumference in the wide portion of said generally cone-shaped main piece; said ring comprising a plurality of apertures providing direct fluid connection between said interior space and points external to said generally cone-shaped main piece; a fluid supplying mechanism (FSM), said FSM in continuous fluid communication with (i) an anesthetization gas inlet positioned outside said ELSM and an outlet located within said ELSM; (ii) an air suction scavenging device positioned outside said ELSM and said mask, and an air suction outlet located within said ELSM; and (iii) a plurality of air conditioning tubes; an airtight shell, said airtight shell adapted to (i) prevent leakage of anesthetization gas from said ELSM outward to a laboratory; and (ii) avoid accidental spillage of hazardous materials from said airtight ELSM to said laboratory, wherein said airtight shell is adapted to provide thermal isolation between ambient air in said laboratory and air-conditioned animal environment;
 b. placing said AGM in fluid communication with said gas supply inlet;
 c. placing said AGM in fluid communication with a suction gas outlet;
 d. supplying anesthetization gas to said mask via said gas supply inlet; e. placing said AGM in said FSM; and f. enveloping said ELSM in said airtight shell;
wherein, when a mammal's head is positioned in said central opening, said apertures, said interior space and said orifice comprise a direct open fluid connection between said external points, said interior of said mask, and points external to said narrow end, and
wherein said orifice comprises a Bernoulli-type orifice.

* * * * *